(12) United States Patent
Farris et al.

(10) Patent No.: US 9,610,105 B2
(45) Date of Patent: Apr. 4, 2017

(54) MULTI-AXIAL ORTHOPEDIC DEVICE AND SYSTEM

(75) Inventors: Robert A. Farris, Cordova, TN (US); Jeffrey W. Poyner, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/236,383

(22) Filed: Sep. 19, 2011

(65) Prior Publication Data

US 2012/0010661 A1    Jan. 12, 2012

Related U.S. Application Data

(62) Division of application No. 10/922,640, filed on Aug. 20, 2004, now Pat. No. 8,021,397.

(60) Provisional application No. 60/496,536, filed on Aug. 20, 2003.

(51) Int. Cl.
*A61B 17/70* (2006.01)
*A61B 17/00* (2006.01)
*A61B 90/00* (2016.01)

(52) U.S. Cl.
CPC ...... *A61B 17/7037* (2013.01); *A61B 17/7038* (2013.01); *A61B 17/7041* (2013.01); *A61B 17/7011* (2013.01); *A61B 17/7032* (2013.01); *A61B 17/7049* (2013.01); *A61B 2017/00867* (2013.01); *A61B 2090/035* (2016.02)

(58) Field of Classification Search
CPC ..................................... A61B 17/70–17/7046
USPC .......................................... 606/246, 264–279
See application file for complete search history.

(56) References Cited

U.S. PATENT DOCUMENTS

| 4,085,744 A | 4/1978 | Lewis et al. |
| 4,404,967 A | 9/1983 | Bacal et al. |
| 4,611,582 A | 9/1986 | Duff |
| 4,763,644 A | 8/1988 | Webb |
| 4,805,602 A | 2/1989 | Puno et al. |
| 4,841,959 A | 6/1989 | Ransford |
| 4,867,144 A | 9/1989 | Karas et al. |

(Continued)

FOREIGN PATENT DOCUMENTS

| DE | 195 09 332 | 8/1996 |
| DE | 197 20 782 | 11/1998 |

(Continued)

OTHER PUBLICATIONS

Protest under 37 C.F.R. Section 1.291, dated Mar. 3, 1997.

(Continued)

*Primary Examiner* — Jan Christopher Merene
*Assistant Examiner* — Steven Cotroneo

(57) ABSTRACT

Embodiments of an orthopedic implant device and system, and methods for implanting them, are disclosed. The implant may include a receiver member having a channel for accommodating an elongated rod or other longitudinal member, a bone anchoring member such as a screw or hook, and a base member rotatable with respect to the receiver member for retaining the bone anchoring member in the receiver member. The base member is configured to allow at least two different degrees of maximum angulation of the bone anchoring member with respect to the receiver member. The number and relative direction of such angulations are independent of the orientation of the channel or other part of the receiving member.

17 Claims, 12 Drawing Sheets

(56) References Cited

U.S. PATENT DOCUMENTS

| | | |
|---|---|---|
| 4,887,595 A | 12/1989 | Heinig et al. |
| 4,946,458 A | 8/1990 | Harms et al. |
| 5,005,562 A | 4/1991 | Cotrel |
| 5,024,213 A | 6/1991 | Asher et al. |
| 5,084,049 A | 1/1992 | Asher et al. |
| 5,085,660 A | 2/1992 | Lin |
| 5,092,893 A | 3/1992 | Smith |
| 5,108,395 A | 4/1992 | Laurain |
| 5,133,716 A | 7/1992 | Plaza |
| 5,147,360 A | 9/1992 | Dubousset |
| 5,154,718 A | 10/1992 | Cozad et al. |
| 5,176,678 A | 1/1993 | Tsou |
| 5,207,678 A | 5/1993 | Harms et al. |
| 5,261,907 A | 11/1993 | Vignaud et al. |
| 5,261,909 A | 11/1993 | Sutterlin et al. |
| 5,312,405 A | 5/1994 | Korotko et al. |
| 5,330,477 A | 7/1994 | Crook |
| 5,360,431 A | 11/1994 | Puno et al. |
| 5,364,399 A | 11/1994 | Lowery et al. |
| 5,368,594 A | 11/1994 | Martin et al. |
| 5,437,671 A | 8/1995 | Lozier et al. |
| 5,439,463 A | 8/1995 | Lin |
| 5,443,465 A | 8/1995 | Pennig |
| 5,443,467 A | 8/1995 | Biedermann et al. |
| 5,466,237 A | 11/1995 | Byrd, III et al. |
| 5,470,333 A | 11/1995 | Ray |
| 5,474,555 A | 12/1995 | Puno et al. |
| 5,476,464 A | 12/1995 | Metz-Stavenhagen et al. |
| 5,498,262 A | 3/1996 | Bryan |
| 5,498,263 A | 3/1996 | DiNello et al. |
| 5,501,684 A | 3/1996 | Schlapfer et al. |
| 5,520,690 A | 5/1996 | Errico et al. |
| 5,527,314 A | 6/1996 | Brumfield et al. |
| 5,531,746 A | 7/1996 | Errico et al. |
| 5,545,164 A | 8/1996 | Howland |
| 5,549,607 A | 8/1996 | Olson et al. |
| 5,549,608 A | 8/1996 | Errico et al. |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,593,408 A * | 1/1997 | Gayet et al. .................. 606/261 |
| 5,601,552 A | 2/1997 | Cotrel |
| 5,601,553 A | 2/1997 | Trebing et al. |
| 5,607,426 A | 3/1997 | Ralph et al. |
| 5,609,593 A | 3/1997 | Errico et al. |
| 5,609,594 A | 3/1997 | Errico et al. |
| 5,643,265 A | 7/1997 | Errico et al. |
| 5,647,873 A * | 7/1997 | Errico et al. .................. 606/264 |
| 5,651,789 A | 7/1997 | Cotrel |
| 5,667,507 A | 9/1997 | Corin et al. |
| 5,669,910 A | 9/1997 | Korhonen et al. |
| 5,669,911 A | 9/1997 | Errico et al. |
| 5,672,176 A * | 9/1997 | Biedermann et al. ........ 606/271 |
| 5,688,272 A | 11/1997 | Montague et al. |
| 5,688,273 A | 11/1997 | Errico et al. |
| 5,690,630 A | 11/1997 | Errico et al. |
| 5,702,393 A | 12/1997 | Pfaifer |
| 5,707,372 A | 1/1998 | Errico et al. |
| 5,709,684 A | 1/1998 | Errico et al. |
| 5,716,355 A | 2/1998 | Jackson et al. |
| 5,725,588 A | 3/1998 | Errico et al. |
| 5,733,286 A | 3/1998 | Errico et al. |
| 5,752,955 A | 5/1998 | Errico |
| 5,810,818 A | 9/1998 | Errico et al. |
| 5,817,094 A | 10/1998 | Errico et al. |
| 5,876,402 A | 3/1999 | Errico et al. |
| 5,879,351 A | 3/1999 | Viart |
| 5,885,284 A | 3/1999 | Errico et al. |
| 5,885,286 A | 3/1999 | Sherman et al. |
| 5,947,966 A | 9/1999 | Drewry et al. |
| 5,980,523 A | 11/1999 | Jackson |
| 6,015,409 A | 1/2000 | Jackson |
| 6,077,263 A | 6/2000 | Ameil et al. |
| 6,080,156 A | 6/2000 | Asher et al. |
| 6,113,600 A | 9/2000 | Drummond et al. |
| 6,113,601 A * | 9/2000 | Tatar ........................... 606/266 |
| 6,132,431 A * | 10/2000 | Nilsson et al. ............... 606/261 |
| 6,132,432 A * | 10/2000 | Richelsoph .................. 606/278 |
| 6,136,003 A | 10/2000 | Van Hoeck et al. |
| 6,217,578 B1 | 4/2001 | Crozet et al. |
| 6,280,442 B1 | 8/2001 | Barker et al. |
| 6,540,748 B2 | 4/2003 | Lombardo |
| 6,660,004 B2 * | 12/2003 | Barker et al. ................. 606/328 |
| 8,257,398 B2 * | 9/2012 | Jackson ....................... 606/264 |
| 2001/0047171 A1 | 11/2001 | Troxell et al. |
| 2002/0026193 A1 * | 2/2002 | Barker ............... A61B 17/7037 606/328 |
| 2002/0058942 A1 * | 5/2002 | Biedermann et al. ........... 606/73 |
| 2003/0032957 A1 | 2/2003 | McKinley et al. |
| 2003/0055426 A1 | 3/2003 | Carbone et al. |
| 2003/0153911 A1 * | 8/2003 | Shluzas ......................... 606/61 |
| 2003/0167058 A1 * | 9/2003 | Shluzas ......................... 606/61 |
| 2004/0116928 A1 | 6/2004 | Young et al. |
| 2004/0116929 A1 * | 6/2004 | Barker et al. .................. 606/61 |
| 2004/0153077 A1 * | 8/2004 | Biedermann et al. ........... 606/73 |
| 2004/0236330 A1 * | 11/2004 | Purcell et al. .................. 606/61 |
| 2004/0267264 A1 * | 12/2004 | Konieczynski et al. ........ 606/73 |

FOREIGN PATENT DOCUMENTS

| | | |
|---|---|---|
| FR | 2 794 637 A1 | 12/2000 |
| GB | 2 173 104 A | 10/1996 |
| WO | WO 96/39090 | 12/1996 |
| WO | WO 00/76413 | 12/2000 |
| WO | WO 02/30307 | 4/2002 |

OTHER PUBLICATIONS

Declaration of J.P. Errico Pursuant to Protest Under 37 C.F.R. Section 1.291.

Sofamor Danek Meeting May 2, 1996, entitled Implemedics.

* cited by examiner

MULTI-AXIAL ORTHOPEDIC DEVICE AND SYSTEM

REFERENCE TO RELATED APPLICATIONS

This application is a divisional of co-pending U.S. patent application Ser. No. 10/922,640 filed Aug. 20, 2004, U.S. Pat. No. 8,021,397 which claims benefit of Provisional 60/496,536 filed on Aug. 20, 2003.

FIELD OF THE INVENTION

The disclosed subject matter generally relates to implants used for correction of orthopedic injuries or deformities, and more specifically, but not exclusively, concerns apparatuses and methods for fixing a portion of the spine to allow correction or healing thereof.

BACKGROUND

In the realm of neurologic, orthopedic and spinal surgery, it is well known to use implants to fix the position of bones. In this way, the healing of a broken bone can be promoted, and malformations or other injuries can be corrected. For example, in the field of spinal surgery, it is well known to place such implants into vertebrae for a number of reasons, including (a) to correct an abnormal curvature of the spine, including a scoliotic curvature, (b) to maintain appropriate spacing and provide support to broken or otherwise injured vertebrae, and (c) to perform other therapies on the spinal column.

Typical implant systems include several pieces, which may be associated or useful with only specific other pieces. Among such pieces are screws, hooks rods, plates and similar longitudinal members for supporting, holding and/or correcting one or more bones. Such longitudinal members can be fastened to bones via direct or indirect connection to hooks, screws, bolts or other fasteners, and can be linked to each other by a variety of connectors. In the spinal field, for example, screws or other fasteners can be attached to two or more vertebrae, the vertebrae can be adjusted into their normal or a therapeutically better position, and longitudinal members are connected to the fasteners so that the vertebrae are held in the normal or therapeutically improved position. Interbody devices, such as intervertebral cages or spacers to maintain the space and positioning of two adjacent vertebrae with respect to each other are also known.

Accordingly, known bone screws, hooks, clamps and other bone fasteners or fixation devices can be connected or adjoined to a particular bone or bones as a connection between the remainder of the implant and the bone(s). Specially formed plates or rods are commonly used as stabilization and support members. Thus, in a common spinal implant system, a spinal plate is implanted along one or more vertebrae by driving a bone screw through the plate and into each of two vertebrae. The vertebrae are thus supported and kept in a particular position by the plate, so as to promote correction or healing.

Where a rod is used as a support and stabilizing member, commonly a series of two or more screws are inserted into two or more vertebrae to be instrumented. A rod is then placed within or coupled to the heads of the screws, or is placed within a connecting device that links the rod and a screw head, and the connections are tightened. In this way, a rigid supporting structure is fixed to the vertebrae, with the rod providing the support that maintains and/or promotes correction of the vertebral malformation or injury.

Many varieties of bone fixation devices (e.g. screws and hooks) are monoaxial in construction. That is, such devices are connected to the rod or plate such that a longitudinal axis through the rod or plate and a longitudinal axis through the fixation device are capable of only a single position with respect to each other. While useful in certain circumstances, in some therapeutic situations such an inflexible device is impractical, or can lead to a longer duration of surgery.

More recently, bone fixation devices having multi-axial capability have been introduced. Examples of such constructs are shown in U.S. Pat. Nos. 5,797,911, 5,954,725, and 6,280,445. These devices allow one or more degrees of freedom between a fastening portion or fastening member and a receiving portion or member, reducing the required precision of placement of the fixation device, since a head portion of the fixation device is multi-axially positionable around the bone-threaded or hook portion. The head can thus be positioned so as to easily receive the rod, limiting or removing much of the positioning difficulty inherent in prior devices. However, such devices provide a single maximum angle between the fastening portion and the receiving portion for every relative orientation of those parts. Other devices have made possible a larger maximum angle between the fastening portion and the receiving portion when the fastening portion occupies one position with respect to the receiving portion, but allow only a smaller maximum angle when the fastening portion occupies any other position with respect to the fastening portion.

SUMMARY OF THE INVENTION

In one embodiment, the disclosure includes a bone fixation system including a receiver member having a longitudinal axis, a bone anchoring member having a head portion and a bone-engaging portion, the bone anchoring member having at least a first maximum angular position and a second maximum angular position relative to the axis, wherein the second maximum angular position includes a greater angle relative to the axis than the first maximum angular position, and a base member rotatably connected to the receiver member, the base member having at least one wall defining an opening that allows the bone anchoring member to occupy either of the first maximum angular position and the second maximum angular position. The system may also include an elongated member connected to the receiver member.

In another embodiment, an orthopedic implant apparatus is provided including a receiver member having at least one wall defining a channel for receiving at least a portion of an elongated body, the receiver member having a longitudinal axis, a bone anchoring member having a head portion and a hone-engaging portion, and a base member rotatably connected to the receiver member, the base member permitting multi-axial positioning of the bone attachment member with respect to the receiver member. The base member and the bone anchoring member have a first relative position wherein the maximum angle between the bone anchoring member and the axis is a first value. Other relative positions of the base member and the bone attachment member allow a maximum angle between the bone anchoring member and the axis that is less than the first value, and the first relative position is independent of the orientation of the channel of the receiver member.

DESCRIPTION OF THE PREFERRED EMBODIMENTS

Figure 1:
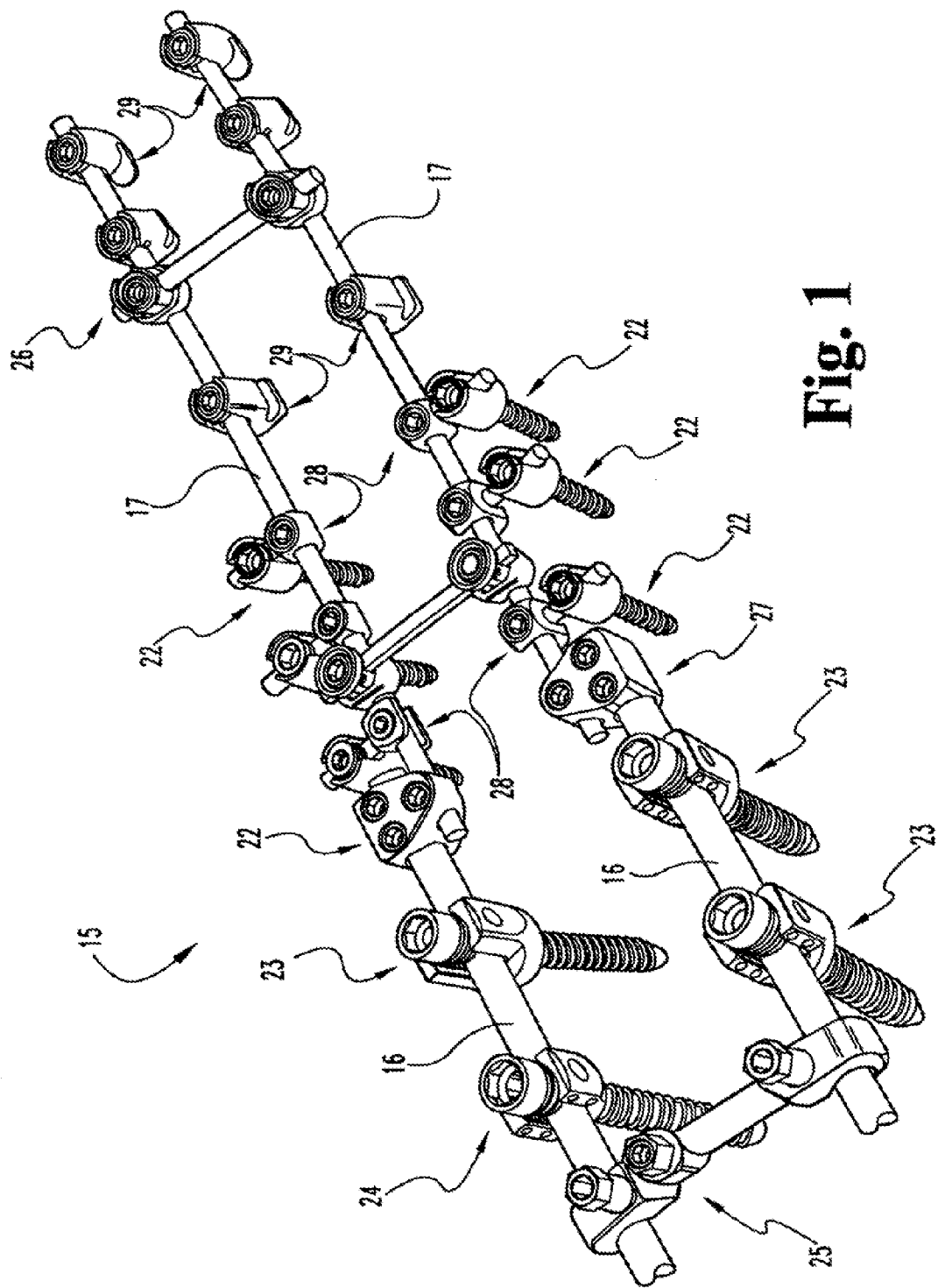
FIG. 1 is a perspective view of an orthopedic implant system according to one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figure 2:
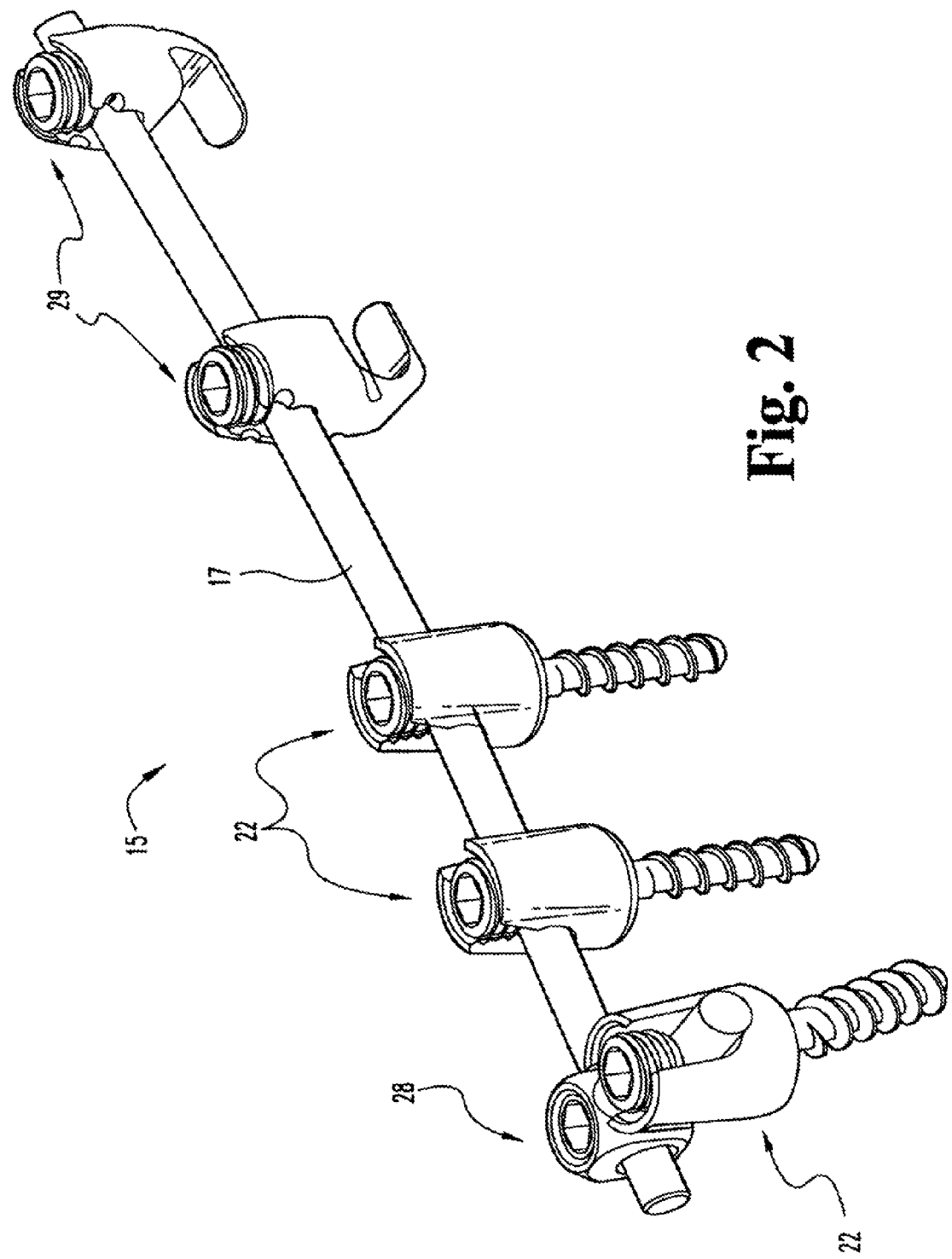
FIG. 2 is a perspective view of a portion of an orthopedic implant system similar to the embodiment of FIG. 1.

Referring generally to FIGS. 1-2, embodiments of a system 15 for orthopedic implantation are shown. Among the possible implants that can be a part of system 15 are longitudinal members such as rods 16, 17, bone attachment members such as screws 22, 23, 24, connectors such as cross connectors 25, 26, longitudinal connector 27, lateral connector 28, hooks 29, and other devices. It will be understood that other types of fasteners or connectors (e.g. clamps) can be used in connection with system 15 or other aspects of the present disclosure. Further additional or alternative longitudinal members can also be used, such as the plates or rods disclosed in U.S. Pat. No. 6,485,491, or the rods disclosed in U.S. Pat. No. 5,217,461, both of which are hereby incorporated herein by reference in their entireties.

As will be described further below, the illustrated embodiments of system 15 can be implanted via an open, minimally-invasive or other surgical approach. Generally, fasteners are inserted into one or more bones, longitudinal members are contoured, if necessary, and surgically inserted and connected to the fasteners. The relative angles of fasteners with respect to the longitudinal member can be adjusted as necessary for ease of connection of the longitudinal member to the fasteners. Connectors are fitted to longitudinal members and/or fasteners as necessary or desired, and all elements are locked against movement with respect to other pans.

Figure 3:
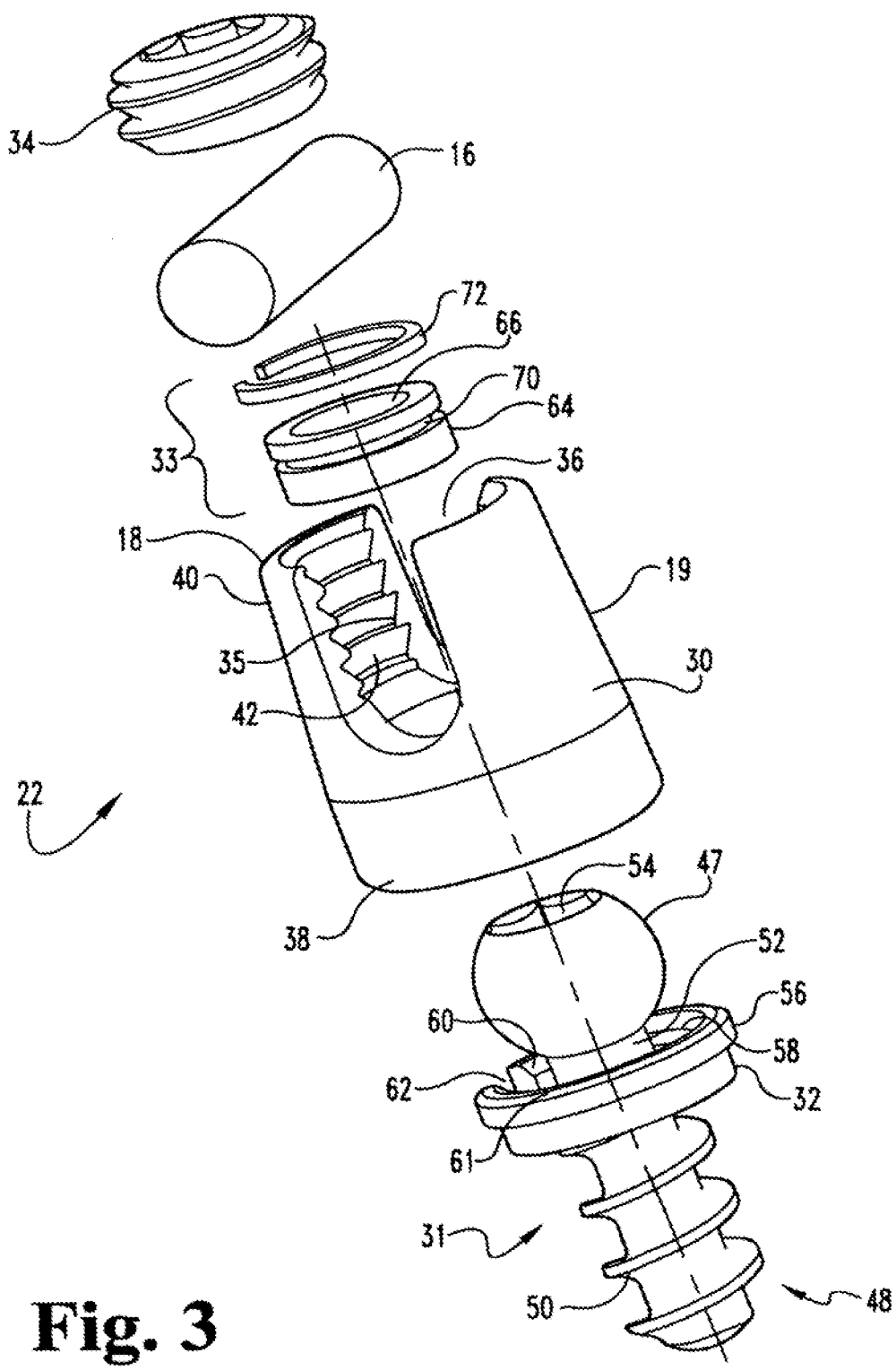
FIG. 3 is an exploded view of an orthopedic implant according to one embodiment of the present invention.
Figure 4:
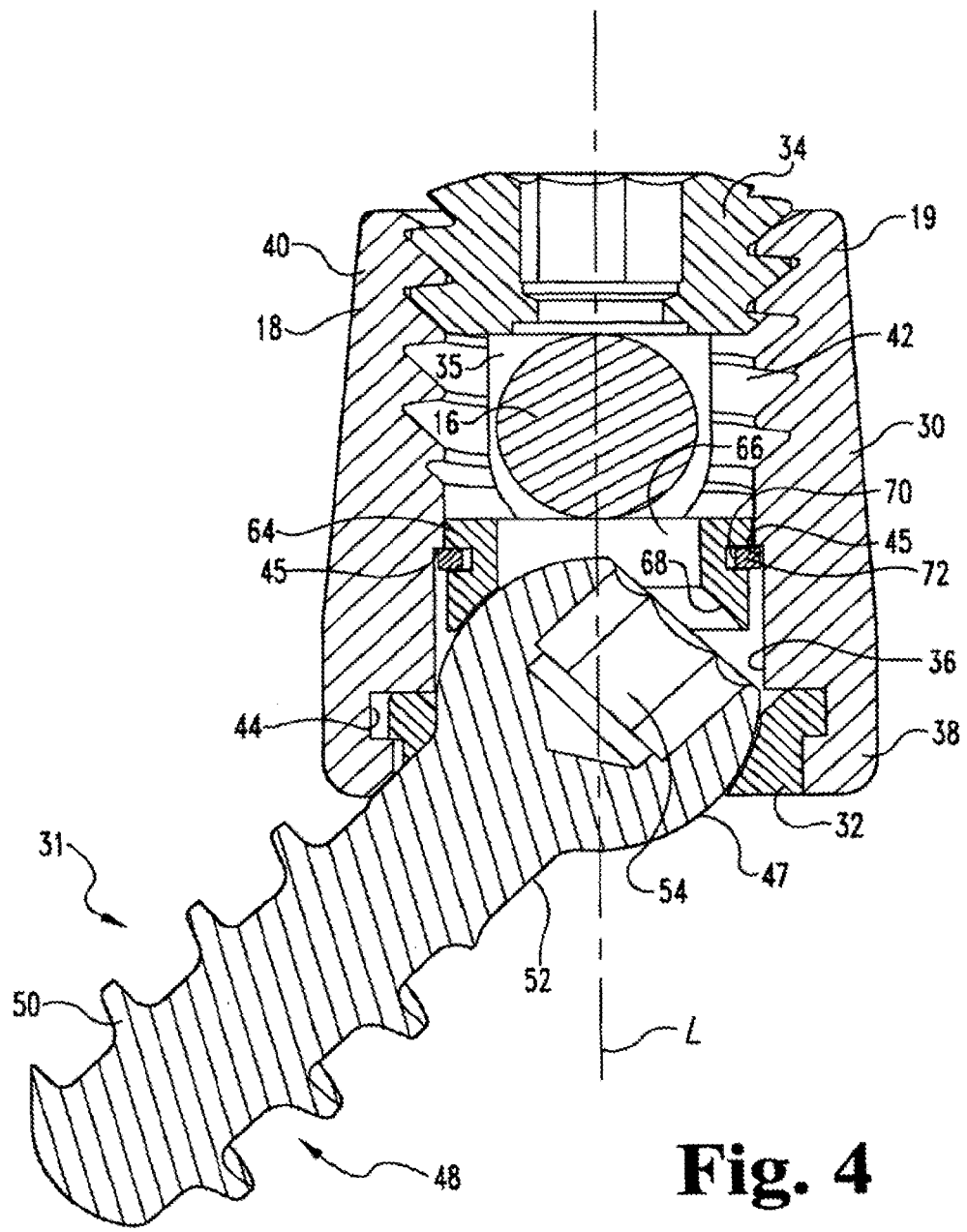
FIG. 4 is a side cross-sectional view of the assembled embodiment of the orthopedic implant shown in FIG. 3.

Referring now generally to FIGS. 3-4, there is shown an embodiment of multi-axial fastener 22. Fastener 22 includes a receiver member 30, a bone anchoring member 31, a base or retaining member 32, a crown assembly 33, and a compression member 34. Receiver member 30 has a channel 35 therethrough adapted to accommodate rod 16 or other longitudinal member. An aperture 36, which may be cylindrical, extends from a lower portion 38 of receiver member 30 transversely to and in communication with channel 35. In a specific embodiment, aperture 36 extends from the lower portion 38 to a top portion 40 of receiver member 30, and aperture 36 has a threaded portion 42 at or near top portion 40 for use when compression member 34 is or includes a set screw or other element with external threads. Threaded portion 42 could be outside of receiver member 30 if an external compression member is used. Alternatively, receiver member 30 could be externally and/or internally configured for compression members using snapping, twisting or other types of closures. The lower portion 38 of receiver member 30 has a groove 44. In the illustrated embodiment, groove 44 extends around the entire circumference of aperture 36.

The illustrated embodiment of receiver member 30 of fastener 22 is an "open backed" variety. That is, channel 35 is open through the top of receiver member 30, making receiver member 30 generally U-shaped and defining two branches 18, 19. It will be understood that the principles of this disclosure apply to "closed backed" fasteners, i.e., those in which a longitudinal member receiving channel is not open through the top of its receiver member, but is essentially a hole through the receiver member. Examples of such "closed backed" fasteners are shown in U.S. Pat. No. 5,005,562, which is incorporated herein by reference.

Figure 5:
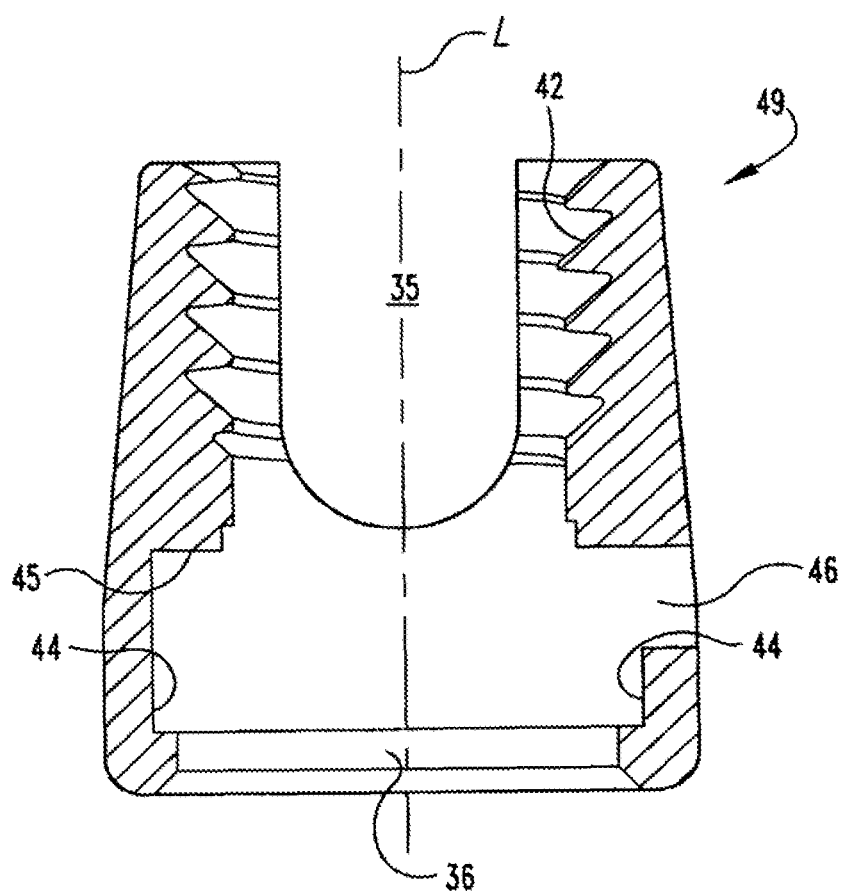
FIG. 5 is a side cross-sectional view of another embodiment of a receiver member useful with the embodiment of the orthopedic implant shown in FIG. 3.
Figure 6:
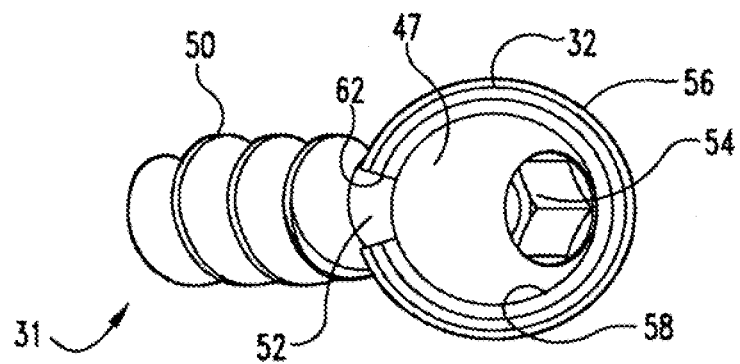
FIG. 6 is a top view of aspects of the embodiment of the orthopedic implant shown in FIG. 3.

A stop surface 45 may be included in receiver member 30 in communication with aperture 36. Stop surface 45 is provided to act as a stop for crown assembly 33 (described below). With stop surface 45, crown assembly 33 cannot move upward in aperture 36 beyond a certain position. Further, referring generally to FIG. 5, a side opening 46 in the side of a specific embodiment of receiver member 49 may be provided to allow insertion of base member 32. Side opening 46 is provided in addition to channel 35, aperture 36 and groove 44, and may be to the side of and transverse to aperture 36 and channel 35. It will be appreciated that side opening 46 could be placed in any part of receiver member 30, such as directly below channel 35. The compressibility or non-compressibility of the base or retaining member 32 to be used may determine the minimum width of side opening 46, as side opening 46 need not be as wide if the base member is compressible.

Bone anchoring member 31, in one embodiment, is a screw element having a head portion 47 and a shank portion 48. Shank portion 48 includes a bone engaging portion 50, which in one particular embodiment has threads, such as for engaging bone tissue, and may also include a non-threaded portion 52. At least part of head portion 47 is preferably, but not necessarily, spherical, rounded, conical, or otherwise configured for rotation or angulation with respect to receiver member 30 and base member 32. A top part of head portion 47 includes an opening 54 for accepting a tool, e.g. a hexagonal opening, for inserting bone anchoring member 31. It will be understood that an alternative bone anchoring member in the form of a hook element is also contemplated. Such a hook includes a head portion identical or similar to head portion 47 of bone anchoring member 31, and a shank portion similar to shank portion 48 of bone anchoring member 31. The shank portion of such a hook would include or extend into a curved portion for engaging or connecting to a bone.

Figure 7:
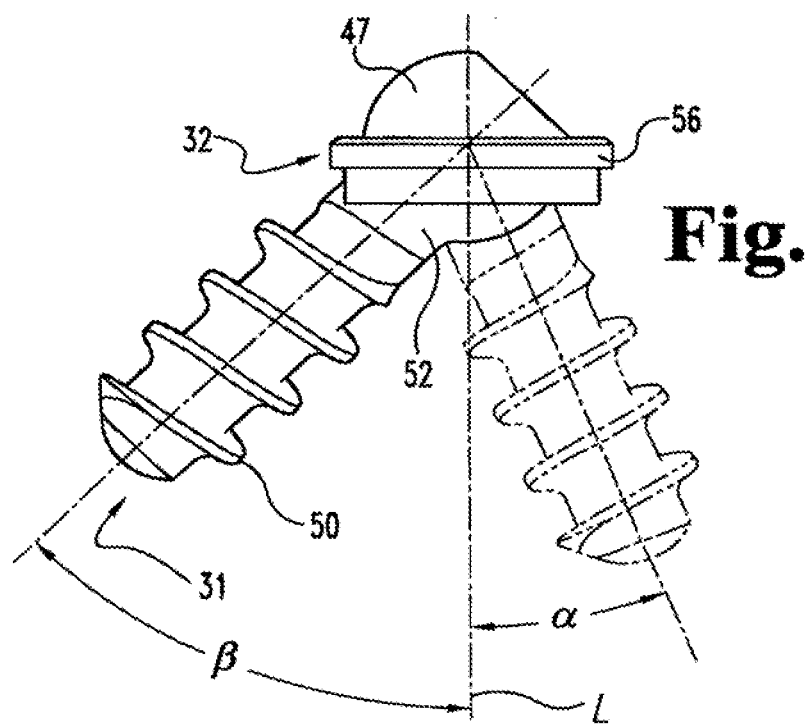
FIG. 7 is a side view of the aspects of the embodiment of the orthopedic implant shown in FIG. 6A.
Figure 8:
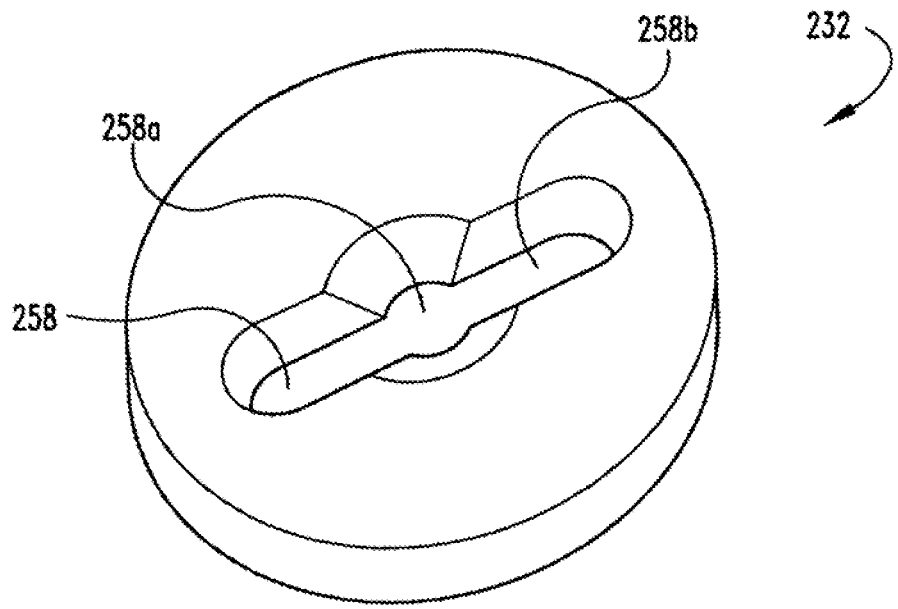
FIG. 8 is a perspective view of an embodiment of a base or retaining member useable with the embodiment of an orthopedic implant shown in FIG. 3.
Figure 9:
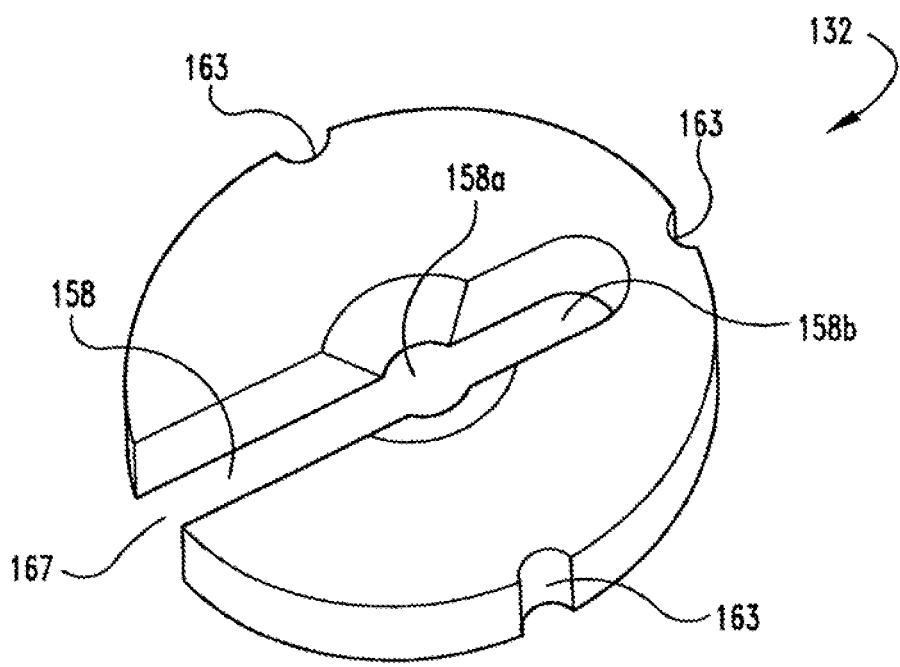
FIG. 9 is a perspective view of another embodiment of a base or retaining member useable with the embodiment of an orthopedic implant shown in FIG. 3.

Base or retaining member 32, 132, 232 in the embodiments shown in FIGS. 3, 4 and 6-9 are similar. Referring generally to base member 32, it is substantially circular in one embodiment with a flange 56 and a center opening 58. Center opening 58 is bounded by walls 60, 61. As examples, walls 60, 61 may be a portion of a cone or sphere, or may form a sharp edge. The embodiments of base members 32 and 132 generally form a C-shaped element (FIGS. 3-4, 6-7 and 9), and the embodiment of base member 232 generally forms the entirety of a circle (FIG. 8). Base member 32 includes a gap 62 in its circumference along with a center opening 58. Opening 58 is shown in one embodiment as substantially circular, but could also have a conical, spherical, stepped, recessed, and/or other configuration. Opening 58 allows head portion 47 of bone anchoring member 31 to rotate with respect to base member 32, allowing positioning of bone anchoring member 31 at any of a variety of angles with respect to longitudinal axis L (FIG. 4) of receiver member 30.

Referring to FIG. 7, it will be noted that the interference of base member 32 and shank portion 48 of bone anchoring member 31 determines a first maximum angle α between bone anchoring member 31 and axis L for at least a portion of the relative positions of bone anchoring member 31 and base member 32. Gap 62 acts as a slot or elongation of center opening 58, so that when bone anchoring member 31 is oriented so that shank portion 48 is substantially aligned with gap 62, a second, larger maximum angle β between bone anchoring member 31 and axis L is available because interference between shank 48 and base member 32 is either eliminated or moved outward. In other words, gap 62 provides space in which at least a part of shank portion 48 can extend to provide a greater maximum angle β. A wider gap 62, for example a gap 62 that is larger than the diameter of shank portion 48 of bone anchoring member 31, allows shank portion 48 to extend through gap 62, and the maximum angle β in that instance is limited only by interference between shank portion 48 and receiver member 30. A narrower gap 62 allows only a part of shank portion 48 into gap 62, and thus the maximum angle β is limited by the points of interference between shank portion 48 and the edges of base member 32 adjacent gap 62. The magnitude of maximum angle β is therefore a function of the width of gap 62.

In the solid-circumference embodiment of base member 232 (FIG. 8), center opening 258 also has a circular portion 258a and an elongated or slot portion 258b. When bone anchoring member 31 is used with base member 232, there is a first maximum angle between bone anchoring member 31 and axis L when bone anchoring member 31 is not substantially aligned with slot portion 258b. A second larger maximum angle is available when bone anchoring member 31 is substantially aligned with at least part of slot portion 258b. Similar to the discussion above with respect to gap 62, it will be seen that the magnitude of that second larger maximum angle is a function of the width and length of slot portion 258b. The embodiment of base member 232 in FIG. 8 is shown without one or more flanges. It will be understood that such flange(s) as flange 52 could be provided for this embodiment as well. The embodiment of base member 132 (FIG. 9) combines features of base members 32 and 232.

Base member 132 is essentially the same as base member 232, with the exception that a gap 162 is provided. Gap 162 can further allow base member 132 to be radially compressed, e.g. for insertion into groove 44 of receiver member 30, or to be radially expanded. In embodiments that are to be radially compressed or expanded, e.g. base member 32, 132, one or more notches or indentations 163 (FIG. 9) may be provided around the outer side surface of base member 132. In a particular embodiment, three such notches 163 may be provided, one placed substantially diametrically opposite gap 162, and the remaining two notches 163 placed approximately about 90 degrees from either side of the first notch 163, or approximately about equidistant between the first notch 163 and gap 162. Such notch(es) 163 provide stress relief for base member 132, reducing or eliminating the risk that base member 132 will not return to its original shape after radial compression or expansion. It will be noted that one or more notches similar or identical to notches 163 can be incorporated into other C-shaped embodiments such as base member 32.

Base members 32, 132, 232 may also be configured with one or more undulating or wavy portions. An example of such an undulating ring is seen in FIG. 17a of U.S. Pat. No. 6,485,491. Such undulating portions are preferably sufficiently thin to enable embodiments of base members 32, 132, 232 that include them to elastically flatten. These embodiments can act as a type of spring, exerting a force on the head portion 47 of bone anchoring member 31. Such force may hold head portion 47 against crown assembly 33 (if present), or another part of receiver member 30. Looseness or "slack" in the fastener 22 can thus be reduced or substantially eliminated, without preventing all movement of head portion 47. When fastener 22 is locked as described below, the opposing force on head portion 47 may flatten any undulating portions of a base member 32, 132, 232 partially or completely.

Crown assembly 33, in the embodiment shown in FIG. 3, includes at least a crown element 64, which is preferably substantially cylindrical with an internal opening 66 and an undersurface 68. Crown element 64 is sized to fit within aperture 36 of receiver member 30, so that crown element 64 has some freedom of axial movement within aperture 36. Internal opening 66 is provided to allow access to tool opening 54 in bone anchoring member 31 when crown element 64 is above or atop bone anchoring member 31. Undersurface 68 is preferably configured to accommodate at least a part of head portion 47 of bone anchoring member 31. For example, undersurface 68 may be shaped (e.g. spherical, rounded, conical, or otherwise) to allow relative movement between crown element 64 and part or all of head portion 47 of bone anchoring member 31. In the embodiment in which both undersurface 68 and head portion 47 have a rounded or spherical portion, undersurface 68 may have substantially the same diameter as head portion 47. Further, crown element 64 may include an external groove 70, and crown assembly 33 may also include a C-shaped snap-ring 72 adapted to fit at least partially within groove 70. Snap-ring 72 assists in base crown element 64 within receiver member 30 by interfering with stop surface 45 in receiving member 30.

Snap-ring 72 may also be configured with one or more undulating or wavy portions. Such undulating portions are preferably sufficiently thin to enable embodiments of snap-ring 72 that include them to elastically flatten. These embodiments can act as a type of spring between receiver member 30 (e.g. stop surface 45) and crown element 64, exerting a force on the crown element 64. Such force may hold crown element 64 against head portion 47 of bone anchoring member 31 or against a part of receiver member 30 (if bone anchoring member 31 is not yet within receiver member 31). Looseness or "slack" in the fastener 22 can thus be reduced or substantially eliminated, without preventing all movement of crown element 64. When fastener 22 is locked as described below, the forces on crown element 64 may flatten any undulating portions of snap-ring 72 partially or completely.

Compression member 34 is shown in one embodiment as an externally threaded element. Compression member 34 may be a standard set screw or a break-offset screw such as those disclosed in U.S. Pat. No. 6,478,795, the entirety of which is incorporated herein by reference. Compression member 34 may also include reverse angle threads as disclosed in U.S. Pat. No. 6,296,642, the entirety of which is incorporated herein by reference. In the threaded embodiment, compression member 34 is configured to thread into threaded portion 42 of receiver member 30 and against rod 16, to compress crown element 64 and lock fastener 22 with respect to rod 16. Alternatively or additionally, compression member 34 can include an external element such as a nut or cap, which may have threads or other features for holding the external element to receiver member 30. If an external element is used, receiver member 30 may be provided with compatible threads or other features for mating with the external element.

Figure 10:
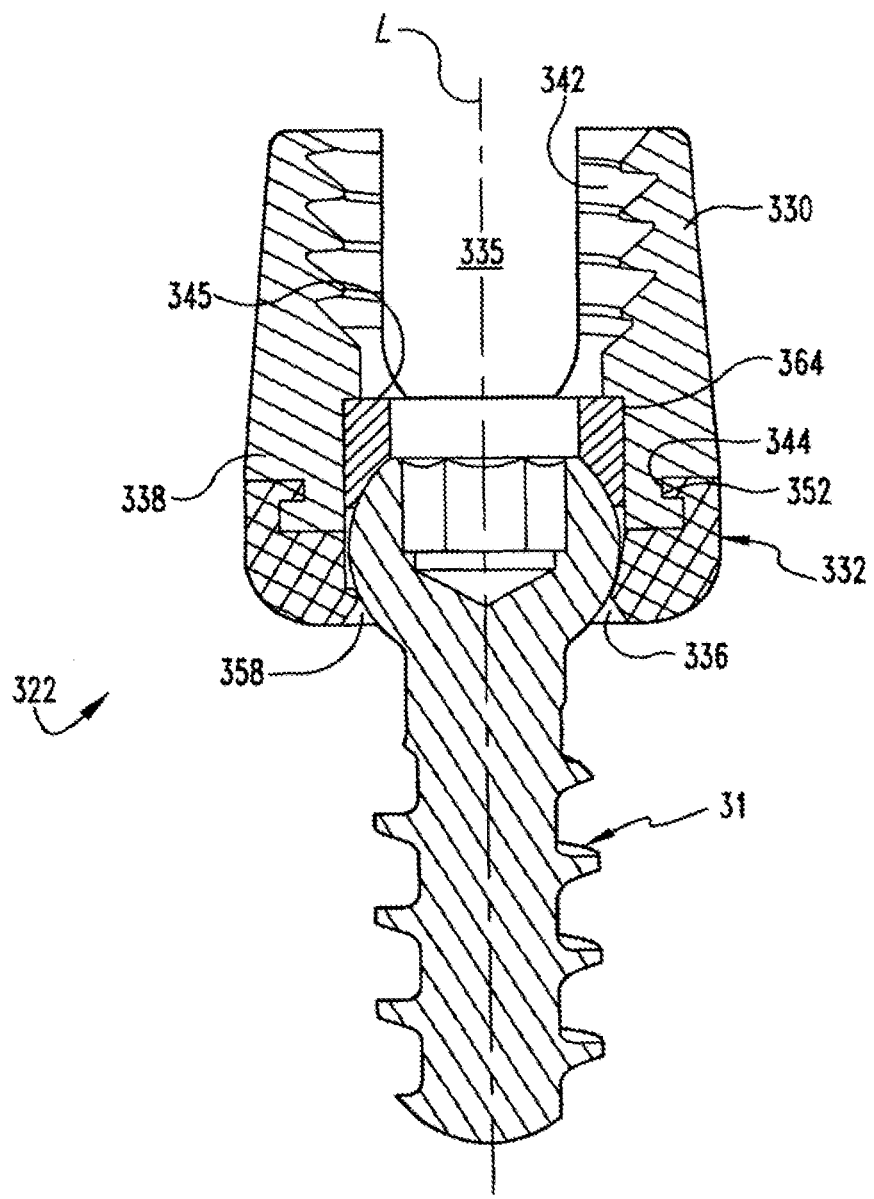
FIG. 10 is a side cross-sectional view of an orthopedic implant according to another embodiment of the present invention.
Figure 11:
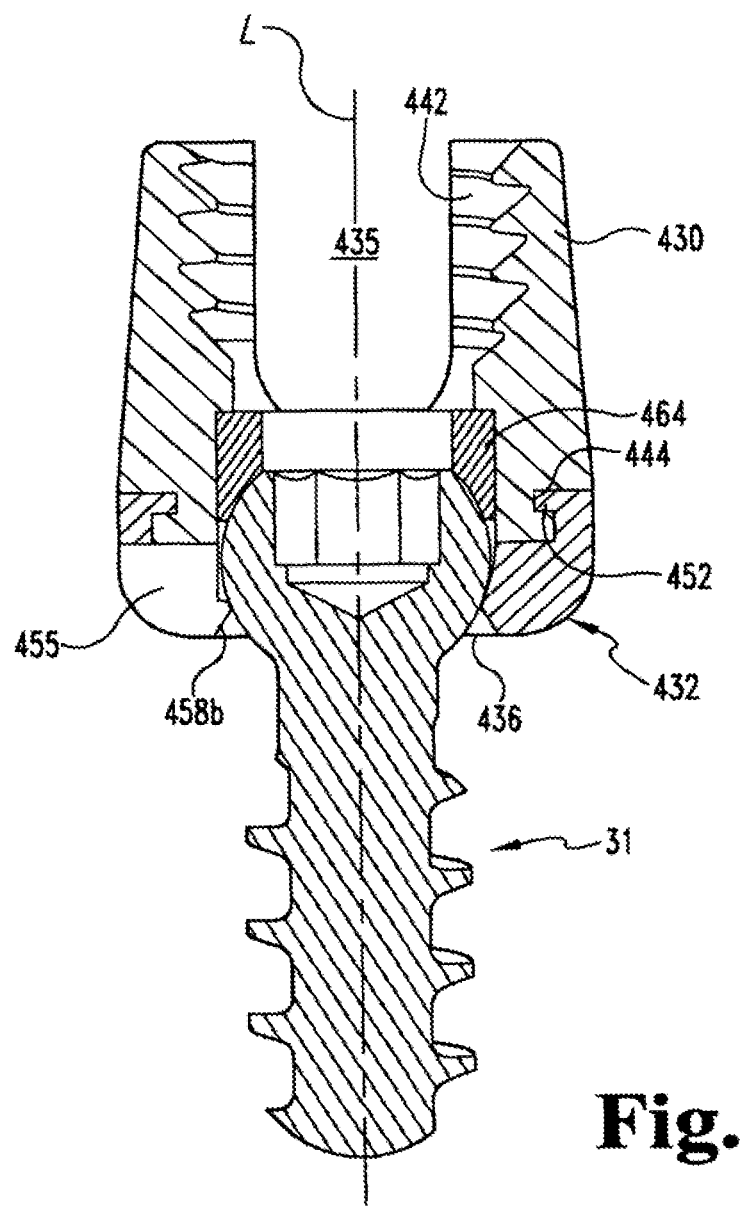
FIG. 11 is a side cross-sectional view of an orthopedic implant according to yet another embodiment of the present invention.
Figure 12:
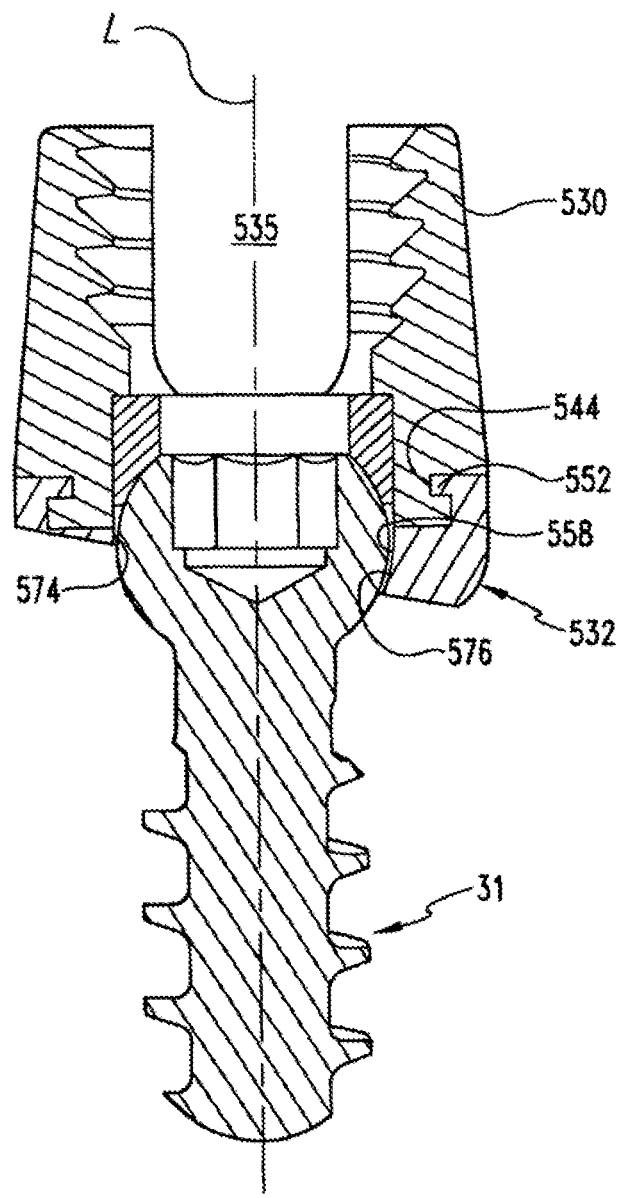
FIG. 12 is a side cross-sectional view of an orthopedic implant according to still another embodiment of the present invention.

Alternative embodiments of a receiver member and a base member are depicted in FIGS. 10-12. Throughout this disclosure, related features are indicated by replacing or adding a new first digit to the numbers identified above. Referring to FIG. 10, receiver member 330 and base member 332 can be used with the elements described above in a multi-axial fastener similar to fastener 22, or in other orthopedic implants. Receiver member 330 is shown with channel 335 and aperture 336. It will be appreciated that in one embodiment receiver member 330 can include structure similar or identical in form and purpose to threaded portion 42 and stop surface 45 described above with respect to receiver member 30.

Receiver member 330 and base member 332 are rotatably connected, and such rotatable connection can be achieved in a number of ways. In one embodiment, receiver member 330 includes a groove 344 or thread (not shown). Groove 344 is shown as external of receiver member 330, but it will be understood that such a groove 344 or thread could also be placed inside receiver member 330. Base member 332 in this embodiment includes a circumferential flange 352 or threads (not shown) for rotatable connection to receiver member 330. Base member 332 attaches to receiver member 330 by placing flange 352 into groove 344, preferably in a snap- or press-fit. Where threads are provided on base member 332 and receiver member 330, those threads are engaged to rotatably connect base member 332 and receiver member 330. In the embodiment in which groove 344 is inside receiver member 330, flange 352 will extend outwardly from base member 332, or be otherwise configured to fit with groove 344.

The embodiment of base member 332 depicted in FIG. 10 includes an opening 358 for allowing multi-axial positioning of a bone anchoring member 31. This embodiment of base member 332 allows loading of crown element 64 (and snap-ring 72, if used) through lower portion 338 into aperture 336 of receiver member 330.

Base member 432 can include an opening that permits a larger maximum angle in at least one orientation of the fastener with respect to base member 432 than in other orientations. As shown in FIG. 11, elongated portion 458*b* can extend through the side of base member 432, creating a notch 455. Base member 432 can be rotated with respect to receiver member 430 so that elongated portion 458*b* can be oriented at any of a number of orientations with respect to channel 435 of receiver member 430.

In another embodiment (FIG. 12), opening 558 is non-perpendicular to axis L of aperture 536 of receiver member 530. In this case, there will be a first part 574 of opening 558 that is relatively close to receiver member 530 and a diametrically opposed second part 576 of opening 558 that is relatively distant from receiver member 530. When fastener 31 is oriented so that shank portion 52 is substantially adjacent to first part 574 of opening 558, then the maximum angle of fastener 31 with respect to axis L is greater than a maximum angle afforded by another part of opening 558.

Figure 13:
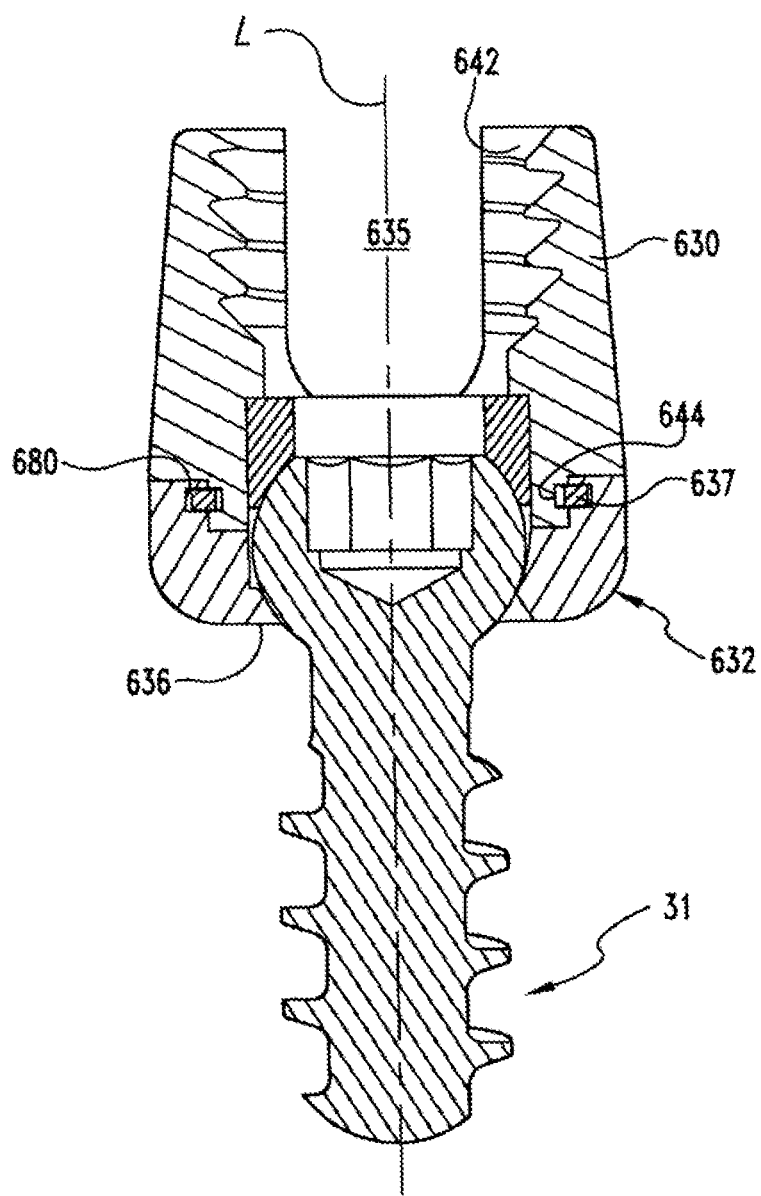
FIG. 13 is a side cross-sectional view of an orthopedic implant according to still another embodiment of the present invention.

Alternatively, the rotatable connection of a receiver member and a base member could be achieved by different structure. For example, receiver member 630 and base member 632 could be rotatably connected via a C-shaped snap-ring 637 (FIG. 13). In this embodiment, receiver member 630 includes a groove 644 in a lower portion, and base member 632 includes a groove 680 in an upper portion. Snap-ring 637 is sized to fit at least partially within grooves 644 and 680, so that a portion of snap-ring 637 extends outside of grooves 644 and 680. To assemble, snap-ring 637 may be placed in one of grooves 644 and 680. Snap-ring 637 may be expanded or contracted as necessary to allow it and the part to which it is connected (receiver member 630 or base member 632) to be connected to the other part so that snap-ring 637 fits at least partially within the other of grooves 644 and 680. When assembled, snap-ring 637 is within at least a part of each groove 644 and 680, thereby holding receiver member 630 and base member 632 together.

Any embodiment of receiver member (e.g. receiver member 630), base member (e.g. base member 632), and/or snap-ring (e.g. snap-ring 637) could be at least partially formed of a shape-memory alloy, such as the nickel-titanium alloy known as Nitinol®. In the embodiment shown in FIG. 13, for example, receiver member 630 and base member 632 may be rotatable until implanted, when the change in temperature of the alloy causes a press or interference fit between them, or snap-ring 637 could expand or contract with a change in temperature to hold receiver member 630 and base member 632 together and/or non-rotatable.

In use, a device such as multi-axial fastener 22 may be implanted as follows. One or more surgical openings are made proximate to an area of the spine or other bones to be instrumented. The surgical openings may be open, minimally-invasive, or of other types that may be known in surgical practice. The vertebrae or other surgical site is prepared, for example by abrading tissue, drilling holes, adjusting bony or other tissue, or other steps to prepare and fixate a bone or bones.

Preferably, prior to insertion of fastener 22, receiver member 30, bone anchoring member 31, base member 32 or 232, and crown assembly 33 (if used) are assembled as described and shown above. In this pre-insertion state, receiver member 30 is multi-axially positionable with respect to bone anchoring member 31, and base member 32 or 232 is rotatable with respect to receiver member 30 so that the elongated or slot portion of opening 58 can point in any direction with respect to receiver member 30. Base member 32 or 232 can be intentionally pre-oriented with respect to receiver member 30 by the assembler prior to surgery, or can simply be placed in groove 44 of receiver member 30 in any orientation. The surgeon is able to change the relative orientation of receiver member 30 with respect to base member 32 or 232 and/or bone anchoring member 31 immediately prior to surgery by rotating bone anchoring member 31 with respect to receiver member 30 and/or base member 32, or by rotating receiver member 30 with respect to base member 32, or both. The surgeon is also able to change those relative orientations during surgery, as further described below. Crown assembly 33 (if present) is held within receiver member 30 between head 47 of fastening member 31 and stop surface 45. It will be appreciated that assembly of these parts can take place at any time prior to insertion, by the surgeon or other person, and that kits including one or more of each type of part described above, in one or more sizes can be provided for the user's convenience.

Once the surgical site is prepared, the assembled implant is inserted into the site and placed. In the embodiment in which bone anchoring member 31 is a screw, threaded shank portion 50 may be inserted into a prepared hole in a vertebra. Where bone anchoring member 31 includes a self-drilling screw or a self-tapping screw, a previously-drilled hole in the bone, or tapping of the hole with a separate tool, may not be necessary. An appropriate tool may be inserted through aperture 36 of receiver member 30 and opening 66 of crown member 64 into tool opening 54 of bone anchoring member 31, and then such tool may be used to turn bone anchoring member 31 to insert it in the bone.

When bone anchoring member 31 is inserted into the bone to the desired depth, the tool is removed, and the surgeon can make adjustments to the orientation of receiver member 30 with respect to bone anchoring member 31 or to the orientation of base member 32 with respect to receiver member 30. For example, the surgeon can turn or angle receiver member 30 with respect to bone anchoring member 31. The surgeon can also turn base member 32 in groove 44 with respect to receiver member 30, for instance by maneuvering receiver member 30 and base member 32 together until a part of bone anchoring member 31 is within an elongated opening in base member 32 such as gap 62, and then turning receiving member 30 with respect to bone anchoring member. Bone anchoring member 31 interferes with base member 32 at gap 62 so that base member 32 cannot turn with receiver member 30. By turning base member 32 with respect to receiver member 30, the orientation of the elongated part of center opening 58 of base member 32 (e.g. gap 62 or slot 158b) rotates or pivots, so that the direction in which bone anchoring member 31 can attain the largest maximum angulation with respect to receiver member 30 is pivotable and independent of the orientation of receiver member 30. Other implant devices, such as additional fasteners 22, multi-axial screws 23, 24, and/or monoaxial hooks 29, can similarly be inserted into the same or other bones.

A longitudinal member, such as spinal rod 16 or 17, can be bent or otherwise contoured and then inserted into the surgical site. The longitudinal member is connected to receiver member 30 by insertion of a portion of it into channel 35 of receiver member 30. The longitudinal member is inserted (or "reduced") at least to a point so that compression member 34 can be connected to receiver member 30 and hold the longitudinal member within channel 35. Similar longitudinal member reduction can be done with respect to other screws, hooks, connectors, clamps or other devices. The surgeon can then manipulate the spine and the implanted devices so that the spine is corrected or placed in a therapeutically improved position.

When the spine and implants are positioned as the surgeon desires, the longitudinal member is locked within receiver member 30 by tightening compression member 34 against the longitudinal member, which presses against crown assembly 33 (if present), fastener member head portion 47, and base member 32. Receiver member 30, particularly channel 35 and its adjoining surfaces, as well as rod 16 or 17 and/or bone anchoring member 31 can be configured so that crown element 64 or crown assembly 33 is not necessary. Other implant devices are similarly tightened to hold the longitudinal member, and the spine, in the desired position.

Figure 14:
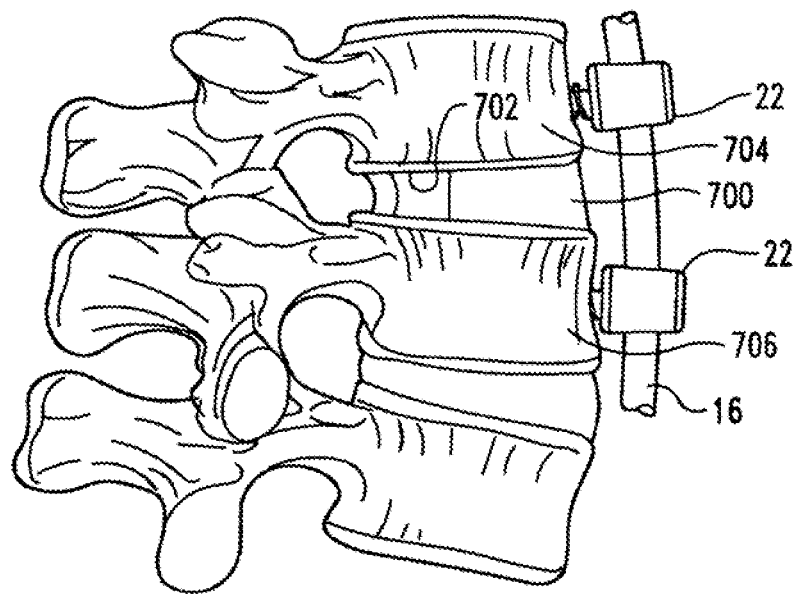
FIG. 14 is a side view of a portion of an orthopedic implant system attached to a part of a spinal column.
Figure 15:
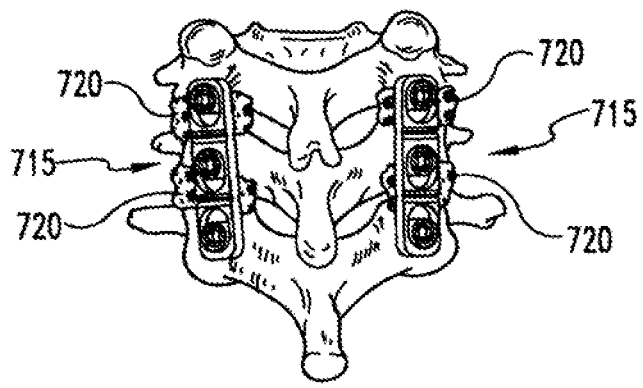
FIG. 15 is a front view of a portion of an orthopedic implant system attached to a part of a spinal column.

As a part of the process of adjusting the position of the spinal column, one or more spacing devices can be inserted between adjacent vertebrae. Examples of such intervertebral implant devices are disclosed in U.S. Pat. Nos. 5,984,967 and 6,113,637, both of which are incorporated herein by reference. "Cage"-type intervertebral implants may also be packed or otherwise provided with one or more substances for inducing or promoting bone growth, such as a bone morphogenic protein, as disclosed in U.S. Pat. No. 5,984,967. Referring to FIG. 14, there is shown a possible embodiment of a fastener 22 connected to a rod 16 as part of a system (such as one of the embodiments of system 15 shown in FIG. 1 or 2), as well as a intervertebral implant 700 placed in the intervertebral disk space 702 between two vertebrae 704, 706. Although FIG. 14 shows the implants placed anteriorly on the spinal column, it is understood that they can be placed posteriorly or in any other appropriate or necessary position. Referring to FIG. 15, there is shown an implant system 715 featuring implants such as those disclosed herein. Bone growth-promoting substance 720, such as BMP (bone morphogenic protein), LMP (LIM mineralization protein), bone chips or marrow or other natural tissue, DBM (demineralized bone matrix), or mesenchymal stem cells, along with any necessary or appropriate carriers or other therapeutic composition, is packed in and/or around the implants and vertebrae.

As seen in FIG. 1, a system 15 can include a set of two rods 16, 17 attached to separate parts of a bone or spinal column. For example, one rod 16 can be attached to a set of vertebrae on one side, and a second rod 16 can be attached to another side of the same vertebrae. These rods can then be connected, for example with cross connector 25. Further, additional smaller rods 17 can be connected via longitudinal connectors 27 to rods 16, and can be fixed to vertebrae (e.g. cervical vertebrae) above the level of the vertebrae to which rods 16 are fixed. It will be appreciated that such longitudinal connection of rods can be accomplished along any contiguous segments of the spinal column, whether cervical, thoracic, lumbar or sacral. It will further be appreciated that, in place of such longitudinal connection of larger and smaller rods, a single rod having a portion with a smaller diameter and a portion with a larger diameter can be used. Such a rod is disclosed in U.S. Pat. No. 5,217,461, incorporated herein by reference.

The structures described above are preferably made of biocompatible materials such as stainless steel, titanium, nickel-titanium (e.g. Nitinol®) or other shape-memory alloys, certain hard plastics or other synthetic materials, and the like.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed is:

1. A bone fixation system, comprising:
   a receiver member having a longitudinal axis and an external bottom surface, said receiver member including an outer surface defining a first groove;
   a bone anchoring member having a head portion and a bone-engaging portion;
   a base member comprising an upper surface engaging said bottom surface to rotatably connect said base member to said receiver member adjacent to said bone anchoring member, said base member including an inner surface defining a second groove, said base member having at least one wall defining a surface that engages said head portion of said bone anchoring member, said wall located below said external bottom surface of said receiver;
   a crown element comprising an undersurface that engages said head portion and an upper surface that engages a transverse flange defined by an inner surface of said receiver member; and
   a ring member occupying at least a portion of said first and second grooves to hold the receiver member and the base member together.

2. The system of claim 1, wherein said wall of said base member further comprises an opening configured to receive a portion of said bone anchoring member such that said bone anchoring member has a greater maximum angle to said longitudinal axis when said bone anchoring member is positioned in a first position of said opening relative to an angle measured between said bone anchoring member and said longitudinal axis when said bone anchoring member is positioned in a second position at a second maximum angle within said opening.

3. The system of claim 2, wherein said wall of said base member is substantially in the form of a C-shaped member defining a gap extending through proximal and distal end surfaces of said base member.

4. The system of claim 1, wherein said receiver member comprises a threaded portion configured to engage threads of a compression member.

5. The system of claim 1, wherein said upper surface extends transverse to said longitudinal axis.

6. The system of claim 1, wherein said crown element is prevented from moving proximally along said longitudinal axis by said transverse flange.

7. A bone fixation system, comprising:
   a receiver member having at least one wall defining a channel for receiving at least a portion of an elongated body and a first groove extending around a longitudinal axis of said receiver, said receiver member including a side surface having an aperture;
   a bone anchoring member having a head portion and a bone-engaging portion, said bone anchoring member having at least a first maximum angular position and a second maximum angular position relative to said receiver member, wherein said second maximum angular position includes a greater angle relative to said receiver member than said first maximum angular position;
   a base member insertable into said receiver member through said aperture, said base member being rotatably connected to said receiver member, said base member having at least one wall defining an opening that allows said bone anchoring member to occupy either of said first maximum angular position and said second maximum angular position, said at least one wall of said base member being substantially in the form of a C-shaped ring and having a second groove extending around a longitudinal axis of the base member; and
   a crown element comprising an undersurface that engages said head portion and an upper surface that engages a transverse flange defined by an inner surface of said receiver member.

8. The system of claim 7 further comprising one or more implants from the group consisting of cross connectors, lateral connectors, monoaxial bone anchoring members, multi-axial bone anchoring members, plate members, and occipital fixators.

9. The system of claim 7, wherein said elongated member is a spinal rod.

10. The system of claim 9, wherein said elongated member is a spinal rod having a substantially constant diameter.

11. The system of claim 9, wherein said elongated member is a spinal rod having a first portion with a first substantially constant diameter and a second portion with a second substantially constant diameter that is larger than said first diameter.

12. An orthopedic implant apparatus comprising:
   a receiver member having at least one wall including an inner surface defining a channel for receiving at least a portion of an elongated body and an outer surface including a groove, said receiver member having a longitudinal axis and a bottom surface defining a bottom receiver plane;
   a bone anchoring member having a head portion and a bone-engaging portion;
   a base member rotatably connected to said receiver member including a first surface that engages said bottom surface and an inwardly facing flange disposed in said groove; and
   a crown element comprising an undersurface that engages said head portion and an upper surface that engages a transverse flange defined by said inner surface,
   wherein said base member permits multi-axial positioning of said bone anchoring member with respect to said receiver member, said base member and said bone anchoring member having a first relative position wherein the maximum angle between said bone anchoring member and said axis is a first value, and wherein other relative positions of said base member and said bone attachment member allow a maximum angle between said bone anchoring member and said axis that is less than said first value, and said first relative position is independent of the orientation of said channel of said receiver member, said base member having a wall configured to engage said head portion of said bone anchoring member, said base wall defining a base plane, said base plane extending below said bottom receiver plane.

13. The apparatus of claim 12, wherein said base member has a lower surface that is non-perpendicular to said axis when said base member is connected to said receiver member.

14. The apparatus of claim 12, wherein said base member has a side wall with a notch, and wherein in said first relative position at least a portion of said bone anchoring member is substantially aligned with at least a portion of said notch.

15. The apparatus of claim 12, wherein said wall of said base member includes an inner surface defining an opening configured for disposal of said head portion, said inner surface of said base member including an inward facing notch extending perpendicular to said longitudinal axis that engages said head portion.

16. The system of claim 12, wherein said receiver member comprises a threaded portion configured to engage threads of a compression member.

17. The system of claim 12, wherein said first surface extends transverse to said longitudinal axis.

* * * * *

UNITED STATES PATENT AND TRADEMARK OFFICE
CERTIFICATE OF CORRECTION

PATENT NO. : 9,610,105 B2
APPLICATION NO. : 13/236383
DATED : April 4, 2017
INVENTOR(S) : Farris et al.

It is certified that error appears in the above-identified patent and that said Letters Patent is hereby corrected as shown below:

In the Specification

Column 2, Line 50, delete "hone-engaging" and insert -- bone-engaging --, therefor.

Column 4, Line 8, delete "pans." and insert -- parts. --, therefor.

Column 5, Line 38, delete "second," and insert -- second --, therefor.

Column 7, Lines 7-8, delete "receiver member 31)." and insert -- receiver member 30). --, therefor.

Column 8, Lines 17-18, delete "fastener 31" and insert -- fastener 22 --, therefor.

Column 8, Line 18, delete "shank portion 52" and insert -- shank portion 48 --, therefor.

Column 8, Line 20, delete "fastener 31" and insert -- fastener 22 --, therefor.

Column 9, Lines 24-25, delete "shank portion 50" and insert -- shank portion 48 --, therefor.

Column 10, Line 33, delete "Although" and insert -- Although, --, therefor.

In the Claims

Column 12, Line 30, Claim 12, delete "apparatus" and insert -- apparatus, --, therefor.

Column 13, Line 9, Claim 16, delete "system" and insert -- apparatus --, therefor.

Column 13, Line 12, Claim 17, delete "system" and insert -- apparatus --, therefor.

Signed and Sealed this
Twentieth Day of February, 2018

Andrei Iancu
*Director of the United States Patent and Trademark Office*